United States Patent [19]

Regel et al.

[11] 4,118,487
[45] Oct. 3, 1978

[54] SUBSTITUTED AZOL-1-YLMETHANES

[75] Inventors: Erik Regel; Wilfried Draber; Karl Heinz Büchel; Manfred Plempel, all of Wuppertal, Germany

[73] Assignee: Bayer Aktiengesellschaft, Germany

[21] Appl. No.: 638,274

[22] Filed: Dec. 5, 1975

[30] Foreign Application Priority Data

Dec. 24, 1974 [DE] Fed. Rep. of Germany ....... 2461406

[51] Int. C.$^2$ .................................................A61K 31/41; C07D 233/56; C07D 233/58; C07D 233/60
[52] U.S. Cl. .................................. 424/232; 260/308 R; 260/465 F; 260/465 G; 260/607 AR; 260/607 B; 260/609 R; 260/611 R; 260/649 R; 260/649 DP; 424/269; 424/273 R; 424/273 P; 548/335; 548/345; 548/373; 568/809; 568/705; 568/807
[58] Field of Search ........................ 260/308 R, 309; 424/269, 273, 232; 548/345, 335

[56] References Cited

U.S. PATENT DOCUMENTS

| 3,801,590 | 4/1974 | Draber et al. | 260/308 R |
| 3,833,603 | 9/1974 | Buchel et al. | 260/309 |
| 3,897,438 | 7/1975 | Draber et al. | 260/308 R |

Primary Examiner—Alton D. Rollins
Attorney, Agent, or Firm—Jacobs & Jacobs

[57] ABSTRACT

Azol-1-ylmethanes substituted on the methane carbon atom by (a) phenyl or lower alkyl and (b) by a biphenyl-4-yl, 4-phenoxyphenyl, 4-phenylthiophenyl, 4-phenylsulfinylphenyl or 4-phenylsulfonylphenyl group are antimycotic and antibacterial agents. The compounds, of which (biphenyl-4-yl)phenyl-imidazol-1-ylmethane is a typical example, are prepared from the correspondingly substituted carbinol through treatment with thionyl-bis-azole or from the correspondingly substituted methyl halide with the azole or a derivative thereof.

53 Claims, No Drawings

SUBSTITUTED AZOL-1-YLMETHANES

The present invention pertains to new azol-1-yl-methanes and their salts, to processes for their preparation and use as medicaments, especially as antimicrobial agents, and to compositions adapted for such use.

It is known that certain N-tritylimidazoles, such as bisphenyl-(2-chlorophenyl)-imidazol-1-ylmethane (clotrimazol), exhibit a good antimycotic action, see e.g. Belgian Pat. No. 720,801. These compounds, and other antimycotic agents generally, do not demonstrate a broad range of activity against other microorganisms.

The present invention provides azol-1-yl-methanes of the general formula

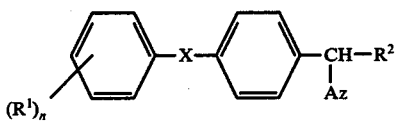

in which
R[1] is hydrogen, halo, haloalkyl, alkyl, alkoxy, nitro or cyano,
R[2] is alkyl or optionally substituted aryl,
X is a single carbon-carbon bond, oxygen, sulphur, thionyl or sulphonyl,
Az is imidazol-1-yl, pyrazol-1-yl, 1,2,4-triazol-1-yl or 1,2,4-triazol-4-yl, and
n is an integer of from 1 to 4,
and salts thereof.

The compounds of Formula I and their salts exhibit powerful antimicrobial action, in particular antimycotic and antibacterial properties. Of the compounds of the invention which are salts thereof, those which are pharmaceutically acceptable are most important and preferred. The azol-1-yl-methanes according to the invention thus show, in addition to a very good and broad antimycotic action, a very powerful antibacterial activity, which is not present ether in known N-tritylimidazoles or in commercially available antimycotic agents such as nystatin, pimaricin or griseofulvin.

In one embodiment, the invention pertains to substituted azol-1-ylmethanes of the formula

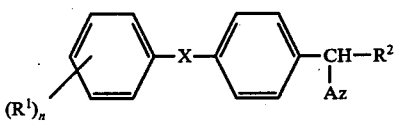

and the pharmaceutically acceptable, nontoxic salts thereof, wherein
R[1] is hydrogen; halo; lower alkyl; lower alkoxy; halo(lower alkyl); phenyl(lower alkyl); nitro; or cyano;
R[2] is lower alkyl; phenyl; or phenyl substituted by from one to three substituents independently selected from the group consisting of lower alkyl, halo, lower alkoxy, lower alkylthio, halo(lower alkyl), nitro or cyano;
X is a carbon-carbon bond; O; S; SO; or SO$_2$;
Az is imidazol-1-yl; pyrazol-1-yl; 1,2,4-triazol-1-yl; or 1,2,4-triazol-4-yl; and
n has a value of from 1 to 4.

In a further embodiment, the invention pertains to compounds of Formula I wherein R[1] is hydrogen; chloro; bromo; lower alkyl; or benzyl.

In a further embodiment, the invention pertains to compounds of Formula I wherein R[2] is lower alkyl; phenyl; or phenyl substituted with one or two substituents selected from the group consisting of chloro, bromo, lower alkyl or trifluoromethyl.

In a further embodiment, the invention pertains to compounds of Formula I wherein Az is imidazol-1-yl.

In a further embodiment, the invention pertains to compounds of formula I wherein X is a carbon-carbon bond or oxygen.

In a further embodiment, the invention pertains to compounds of Formula I wherein Az is imidazol-1-yl; R[1] is hydrogen or chloro; n is 1, 2 or 3; X is a carbon-carbon bond or O; and R[2] is phenyl, chlorophenyl or (lower alkyl)phenyl.

The term lower alkyl denotes a univalent saturated branched or straight hydrocarbon chain containing from 1 to 6 carbon atoms. Representative of such lower alkyl groups are thus methyl, ethyl, propyl, isopropyl, butyl, isobutyl, sec-butyl, tert-butyl, pentyl, isopentyl, neopentyl, tert-pentyl, hexyl, and the like.

The term lower alkoxy denotes a straight or branched hydrocarbon chain of 1 to 6 carbon atoms bound to the remainder of the molecule through a divalent oxygen atom as, for example, methoxy, ethoxy, propoxy, isopropoxy, butoxy, isobutoxy, pentoxy and hexoxy.

The term lower alkylthio denotes a branched or straight hydrocarbon chain of 1 to 6 carbon atoms bound to the remainder of the molecule through a divalent sulfur as, for example, methylthio, ethylthio, propylthio, isopropylthio, butylthio, and the like.

The term halo denotes the monovalent substituents fluoro, chloro, bromo and iodo.

The compounds of the present invention can exist as optical isomers and both the racemates of these isomers and the individual isomers themselves are within the scope of the present invention. The racemates can be separated into their individual isomers through the well known technique such as forming diastereoisomeric salts.

R[1] is preferably straight-chain or branched alkyl of up to 6, in particular 4, carbon atoms, such as methyl, ethyl, isopropyl and tert.-butyl; alkoxy of 1 to 4, especially 1 to 3, carbon atoms, such as methoxy or ethoxy; halo, especially fluoro, chloro and bromo; haloalkyl with up to 4 carbon atoms and up to 5 halo atoms, especially up to 2 carbon atoms and up to 3 like or different halo atoms, in particular, fluoro and chloro, trifluoromethyl being most preferred; or cyano. The number n is preferably 1, 2 or 3. R[2] is preferably straight-chain or branched alkyl with up to 6, especially with up to 4, carbon atoms, examples being methyl, ethyl, isopropyl and tert.-butyl, or optionally monosubstituted or polysubstituted aryl radical with 6 to 10 carbon atoms, especially phenyl. Preferred substituents are halo, especially fluoro, chloro or bromo, straight-chain or branched alkyl with 1 to 6, especially 1 to 4, carbon atoms, alkoxy of 1 to 4 carbon atoms, alkylthio of 1 to 4 carbon atoms and alkylsulfonyl of 1 to 4, especially 1 to 2, carbon atoms, haloalkyl with 1 to 2 carbon atoms and 1 to 5 halogen atoms, especially fluoro and chloro, amino and nitro.

The compounds of the invention are prepared by a process which comprises
(A) treating a carbinol of the formula

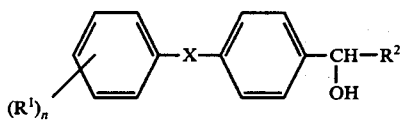

wherein R¹, R², X and n are as herein defined, with a thionyl-bis-azole of the formula Az—SO—Az wherein Az is as herein defined;
(B) treating a substituted halomethane of the formula

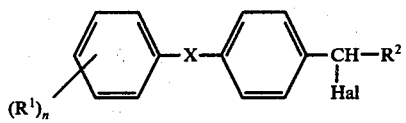

wherein R¹, R², X and n are as herein defined and Hal is chloro or bromo, with (i) an azole of the formula Az—H wherein Az is as herein defined; (ii) an alkali metal or silver salt of said azole, or (iii) a tris(lower alkyl)silane of said azole; and
(C) when desired, converting the product of said treatments to a pharmaceutically acceptable, nontoxic salt of said substituted azol-1-ylmethane or, when said product is an acid addition salt, converting said salt into said substituted azol-1-ylmethane as the free base.

If (4-phenoxyphenyl)-(2-chlorophenyl)-carbinol, thionyl chloride and imidazole are used as starting materials, the course of the first reactions can be represented by the following equation:

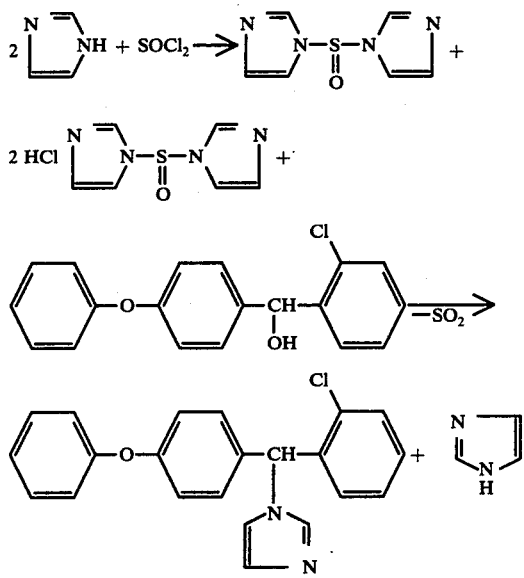

If 4-biphenylyl-phenyl-chloromethane and 1,2,4-triazole are used as starting materials, the course of the second reaction can be represented as follows:

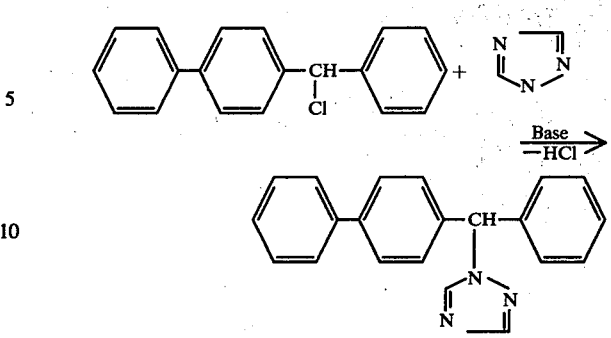

If 4-biphenylyl-(2-chlorophenyl)-bromomethane and sodium imidazole are used as starting materials, the course of the third reaction can be represented as follows:

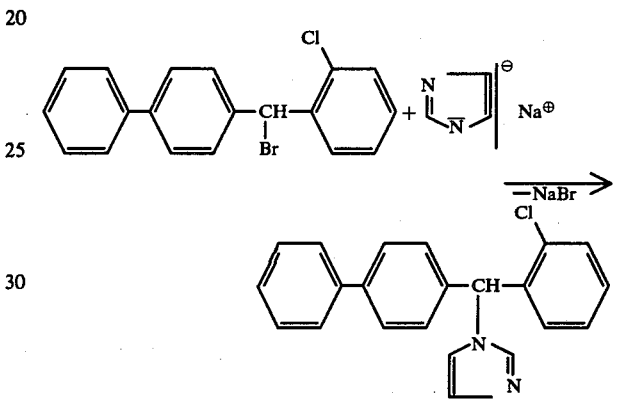

If biphenylyl-phenyl-chloromethane and trimethylsilyl-1-imidazole are used as starting materials, the course of the reaction can be represented as follows:

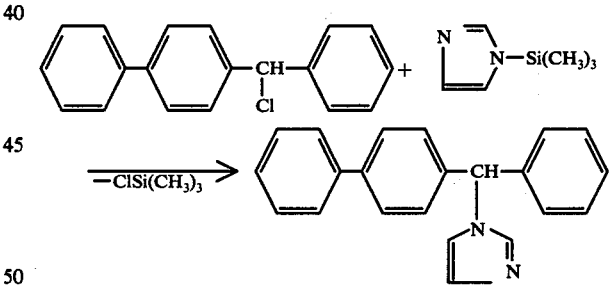

The carbinol starting materials, which can be considered to be α-substituted benzylalcohols, are known or can be readily prepared according to known methods. They can be obtained for example by reduction of the ketones obtained according to a Friedel-Krafts reaction with aluminum isopropylate [see e.g. Izv. Akad. SSSR, 10, 1804 (1962) and Z. obsc. Chim., 34 (3), 977 (1964)] or by a Meerwein-Ponndorf reduction [see e.g., Z. org. Chim., 2 (7), 1288 (1966)]. The reduction can also be carried out with any other reducing agent such as for example sodium borohydride. Ketones can also be reacted with Grignard reagents [see e.g., J. Pharm. Sci. 59 (7), 1042 (1970)] or an appropriate aldehyde can be reacted with Grignard reagents [see e.g. J. Pharm. Sci., 62 (6), 952 (1973) and J. Org. Chem. 36 (18), 2724 (1971)]. The following are examples of suitable carbinols:

(4-phenoxyphenyl)-(2-chlorophenyl)-hydroxymethane
(biphenyl-4-yl)-phenyl-hydroxymethane
(4'-chloro-biphenyl-4-yl)-(4-ethylphenyl)-hydroxymethane
[4-(2-methylphenylthio)-phenyl]-(3-methoxyphenyl)-hydroxymethane
[4-(4'-bromophenylthio)-phenyl]-(4-trifluoromethylphenyl)-hydroxymethane
[4-(2'-methyl-4'-chlorophenylsulfonyl)-phenyl]-(3-bromophenyl)-hydroxymethane
[4-(4'-methoxyphenoxy)-phenyl]-tert.-butyl-hydroxymethane
(4'-trifluoromethylbiphenyl-4-yl)-tert.-butylhydroxymethane
[4-(2,4,6-trichlorophenylthio)-phenyl]-4-tert.-butylphenyl)-hydroxymethane
[4-(2,6-dichlorophenoxy)-phenyl]-phenyl-hydroxymethane
[4-(2,6-dichlorophenoxy)-phenyl]-tert.butyl-hydroxymethane
[4-(2,4,6-trichlorophenoxy)-phenyl]-phenyl-hydroxymethane
[4-(4-chlorophenylthio)-phenyl]-(4-chlorophenyl)hydroxymethane
(4-phenylthiophenyl)-phenyl-hydroxymethane
(4-phenylsulfonylphenyl)-phenyl-hydroxymethane
(biphenyl-4-yl)-(3-methylphenyl)-hydroxymethane
(biphenyl-4-yl)-(3,5-dimethylphenyl)-hydroxymethane
(biphenyl-4-yl)-(4-chlorophenyl)-hydroxymethane
(biphenyl-4-yl)-(2,4-dichlorophenyl)-hydroxymethane
(biphenyl-4-yl)-(4-bromophenyl)-hydroxymethane
(biphenyl-4-yl)-(4-fluorophenyl)-hydroxymethane
(biphenyl-4-yl)-(4-trifluoromethylphenyl)-hydroxymethane
(biphenyl-4-yl)-(4-methylsulfonylphenyl)-hydroxymethane
(2',4'-dichlorobiphenyl-4-yl)-phenyl-hydroxymethane
(2',4',6'-trichlorobiphenyl-4-yl)-phenyl-hydroxymethane
(4'-bromobiphenyl-4-yl)-phenyl-hydroxymethane
[4-(2,6-dichlorophenoxy)-phenyl]-(4-chlorophenyl)-hydroxymethane
(biphenyl-4-yl)-(3-trifluoromethylphenyl)-hydroxymethane
(4'-chlorobiphenyl-4-yl)-(3-trifluoromethylphenyl)-hydroxymethane
(4'-bromobiphenyl-4-yl)-3-trifluoromethylphenyl)hydroxymethane
[4-(2,6-dichlorophenoxy)-phenyl]-(3-trifluoromethylphenyl)-hydroxymethane The halo-methanes starting materials, which can be considered α-substituted benzyl halides, also are known or can be prepared according to conventional methods. They can be prepared for example by halogenation of the foregoing carbinols as with hydrogen chloride [see e.g. J. Org. Chem. 36 (18), 2724 (1971)] or with thionyl chloride [see e.g. Izv. Akad. SSSR, 10 1804 (1962)]. The following are examples of such halo-methanes:

(4-phenoxyphenyl)-(2-chlorophenyl)-chloromethane
biphenyl-4-yl-phenyl-chloromethane
(4'-chlorobiphenyl-4-yl)-(4-ethylphenyl)-chloromethane
[4-(2-methylphenylthio)-phenyl]-(3-methoxyphenyl)-chloromethane
[4-(4-bromophenylthio)-phenyl]-(4-trifluoromethylphenyl)-bromomethane
[4-(2-methyl-4-chlorophenylsulfonyl)-phenyl]-(3-bromophenyL)-bromomethane
[4-(4-methoxyphenoxy)-phenyl]-tert.-butyl-bromomethane
(4-trifluoromethylbiphenyl-4-yl)-tert.-butyl-bromomethane
[4-(2,4,6-trichlorophenylthio)-phenyl]-(4-tert.-butyl-phenyl)-chloromethane
[4-(2,6-dichlorophenoxy)-phenyl]-phenyl-chloromethane
[4-(2,6-dichlorophenoxy)-phenyl]-tert.-butyl-chloromethane
[4-(2,4,6-trichlorophenoxy)-phenyl]-phenyl-chloromethane
[4-(4-chlorophenylthio)-phenyl]-(4-chlorophenyl)-bromomethane
(4-phenylthiophenyl)-phenyl-bromomethane
(4-phenylsulfonylphenyl)-phenyl-bromomethane
(biphenyl-4-yl)-(3-methylphenyl)-bromomethane
(biphenyl-4-yl)-(3,5-dimethylphenyl)-chloromethane
(biphenyl-4-yl)-(4-chlorophenyl)-chloromethane
(biphenyl-4-yl)-(2,4-dichlorophenyl)-chloromethane
(biphenyl-4-yl)-(4-bromophenyl)-chloromethane
(biphenyl-4-yl)-(4-fluorophenyl)-bromomethane
(biphenyl-4-yl)-(4-trifluoromethylphenyl)-bromomethane
(biphenyl-4-yl)-(4-methylsulfonylphenyl)-bromomethane
(2',4'-dichlorobiphenyl-4-yl)-phenyl-bromomethane
(2',4',6'-trichlorobiphenyl-4-yl)-phenyl-chloromethane
(4'-bromobiphenyl-4-yl)-phenyl-chloromethane
[4-(2,6-dichlorophenoxy)-phenyl]-(4-chlorophenyl)-chloromethane
(biphenyl-4-yl)-(3-trifluoromethylphenyl)-chloromethane
(4'-chlorobiphenyl-4-yl)-(3-trifluoromethylphenyl)-bromomethane
(4'-bromobiphenyl-4-yl)-(3-trifluoromethylphenyl)-bromomethane
[4-(2,6-dichlorophenoxy)-phenyl]-(3-trifluoromethylphenyl)-bromomethane Diluents or solvents can optionally be used for the reaction involving the carbinols. These are preferably polar organic solvents, as for example nitriles such as acetonitrile; sulfoxides such as dimethylsulfoxide; amides such as dimethylformamide; ketones such as acetone; ethers such as diethyl ether or tetrahydrofuran, and especially chlorohydrocarbons such as methylene chloride and chloroform. The reaction temperatures can be varied within a substantial range but in general it is between about 0° and about 120° C., preferably 10° to 85° C. In the presence of a solvent, the reaction is advantageously carried out at the boiling point of the solvent. Preferably about 2 mols of the thionyl-bis-azole are employed per mol of the carbinol. The thionyl-bis-azole can be produced in situ. To isolate the product, the solvent is removed by distillation, the residue is taken up in an organic solvent and the solution is washed with water. The organic phase is dried over sodium sulfate and freed from the solvent in vacuo. The product is further purified by recrystallization or salt formation.

For the reaction involving the halomethanes, inert organic solvents can also be used as diluents. These include ketones such as diethyl ketone, acetone and methyl ethyl ketone; nitriles such as propionitrile and acetonitrile; alcohols such as ethanol or isopropanol; ethers such as tetrahydrofuran or dioxane; benzene; amides such as dimethylformamide; halogenated hydrocarbons and hexamethyl-phosphoric acid triamide. When an acid is formed, as in the case of the simple azole, the reaction is preferably carried out in the presence of an acid-binding agent such as alkali metal carbonates, for example sodium carbonate, potassium carbonate and sodium bicarbonate, tertiary lower alkylamines, cycloalkylamines or aralkylamines, for example triethylamine or dimethylbenzylamine; or aromatic or bicyclic amines such as pyridine or diazabicyclooctane. An excess of azole can also serve as the acid-binding agents. The reaction temperatures can be varied within a substantial range here as well. In general, the reaction between the halomethane and free azole is carried out between about 20° and about 150° C., preferably at 80° to 120° C. When a solvent is employed, the reaction can be conducted at the solvent's boiling point. When a salt or the silyl derivative of the azole is employed, reaction temperatures of from about −10° to about 100°, preferably 0° to 85° C., are generally used.

The reactants are employed in approximately molar amounts. When an acid-binding agent is employed, it too is generally present in an equimolar amount.

Isolation of the compounds is performed in the manner described above. Thus any solvent is removed in distillation, the residue is taken up in an organic solvent and the solution is washed with water. The organic phase is dried over sodium sulfate and freed of solvent in vacuo. The product can be further purified by distillation of recrystallization.

Pharmaceutically acceptable salts of these compounds are those of physiologically tolerable acids, as for example the hydrogen halide acids, such as hydrochloric acid and hydrobromic acid, especially hydrochloric acid, sulfuric acid, phosphoric acid, nitric acid, monofunctional and bifunctional carboxylic acids and hydroxycarboxylic acids, such as acetic acid, maleic acid, succinic acid, fumaric acid, tartaric acid, citric acid, salicylic acid, sorbic acid and lactic acid, and organic sulfonic acids such as 1,5-naphthalene-disulfonic acid. Salts can be obtained in a simple manner, in accordance with conventional methods as for example by dissolving the base in a solvent such as diethyl ether and adding the acid, as a gas or as a solution. The salts are isolated in a known manner, as for example by filtration, and be purified if desired.

These azol-1-ylmethanes and their salts exhibit powerful antimycotic properties with a broad spectrum which encompasses dermatophytes, yeasts, Pityrosporum ovale, molds and biphase fungi. They can, therefore, be employed with good success against fungal infections in man and animals such as dermatomycoses and systemic mycoses caused by *Trichophyton mentagrophytes* and other species of Trichophyton, species of Microsporon, *Epidermophyton floccosum*, blastomyces and biphase fungi as well as molds.

Furthermore, the active compounds according to the invention have a low toxicity, are tolerated well, and exhibit strong antibacterial activity against Gram negative and Gram positive bacteria and bacteria-like microorganisms. These properties permit their use not only in medicine, but also for preserving inorganic and organic materials, especially organic materials of all kinds, for example polymers, lubricants, dyestuffs, fibers, leather, paper and timber, foodstuffs, cosmetics such as creams and ointments, and water.

Typical of the pathogens against which these compounds are active are the following:

Micrococcaceae, such as Staphylococci, for example *Staphylococcus aureus, Staph. epidermidis, Staph. aerogenes* and *Gaffkya tetragena* (Staph. = Staphylococcus);

Lactobacteriaceae, such as Streptococci, for example *Streptococcus pyogenes*, α- and β-haemolysing Streptococci, non-(γ-)haemolysing Streptococci, *Str. viridans, Str. faecalis* (Enterococci), *Str. agalactiae, Str. lactis, Str. equi, Str. anaerobis* and *Diplococcus pneumoniae* (Pneumococci) (Str. = Streptococcus);

Neisseriaceae, such as Neisseriae, for example *Neisseria gonorrhoeae* (Gonococci), *N. meningitidis* (Meningococci), *N. catarrhalis* and *N. flava* (N. = Neisseria);

Corynebacteriaceae, such as Corynebacteria, for example *Corynebacterium diphtheriae, C. pyogenes, C. diphtheroides, C. acnes, C. parvum, C. bovis, C. renale, C. ovis* and *C. murisepticum*, Listeria bacteria, for example *Listeria monocytogenes*, Erysipelothrix bacteria, for example *Erysipelothrix insidiosa* and Kurthia bacteria, for example *Kurthia zopfii* (C. = Corynebacterium);

Enterobacteriaceae, such as Escherichiae bacteria of the coli group: Escherichia bacteria, for example *Escherichia coli*, Aerobacter bacteria, for example *A. aerogenes* and *A. cloacae*, Klebsiella bacteria, for example *K. pneumoniae* and *K. ozaenae*, Erwiniae, for example *Erwinia* spec., Serratia, for example *Serratia marcescens* (A. = Aerobacter) (K. = Klebsiella), Proteae bacteria of the Proteus group: Proteus, for example *Proteus vulgaris, Pr. morganii, Pr. rettgeri* and *Pr. mirabilis*, and Providencia, for example *Providencia sp.* (Pr. = Proteus), Salmonelleae: Salmonella bacteria, for example *Salmonella paratyphi* A and B, *S. typhi, S. enteritidis, S. cholera suis* and *S. typhimurium* (S. = Salmonella), Shigella bacteria, for example *Shigella dysenteriae, Sh. ambigua, Sh. flexneri, Sh. boydii* and *Sh. sonnei* (Sh. = Shigella); Pseudomonadeceae, such as Pseudomonas bacteria, for example *Pseudomonas aeruginosa* and *Ps. pseudomallei* (Ps. = Pseudomonas) and Aeromonas bacteria, for example *Aeromonas liquefaciens* and *A. hydrophila* (A. = Aeromonas);

Parvobacteriaceae or Brucellaceae, such as Pasteurella bacteria, for example *Pasteurella multocida, Past. pestis* (Yersinia), *Past. pseudotuberculosis* and *Past. tularensis* (Past. = Pasteurella), Brucella bacteria, for example *Brucella abortus, Br. melitensis* and *Br. suis* (Br. = Brucella), Haemophilus bacteria, for example Haemophilus influenzae, *H. ducreyi, H. suis, H. canis* and *H. aegypticus* (H. = Haemophilus), Bordetella bacteria, for example *Bordetella pertussis* and *B. bronchiseptica* (B. = Bordetella) and Moraxella bacteria, for example *Moraxella lacunata*.

The above list of pathogens is purely by way of example and in no way to be interpreted as imposing a limit.

The invention thus pertains to a method of combatting microbial infections, both mycotic and bacterial, in humans and other warm-blooded animals. These include infectious conditions of the respiratory tracts and the pharyngeal cavity; otitis; pharyngitis; pneumonia; peritonitis; pyelonephritis; cystitis; endocarditis; systemic infections; bronchitis; arthritis and other systemic infections, as well as local bacterial and mycotic infections, as for example of the skin and mucous membranes.

The compounds of the present invention are administered parenterally or orally in any of the usual pharmaceutical forms. These include solid and liquid oral unit dosage forms such as tablets, capsules, powders, suspensions, solutions, syrups and the like, including sustained release preparations, and fluid injectable forms such as sterile solutions and suspensions. The term unit dosage form as used in this specification and the claims refers to physically discrete units to be administered in single or multiple dosage to animals, each unit containing a predetermined quantity of active material in association with the required diluent, carrier or vehicle. The quantity of active material is that calculated to produce the desired therapeutic effect upon administration of one or more such units.

Powders are prepared by comminuting the compound to a suitable fine size and mixing with a similarly comminuted diluent pharmaceutical carrier such as an edible carbohydrate material as for example, starch. Sweetening, flavoring, preservative, dispersing and coloring agents can also be present.

Capsules are made by preparing a powder mixture as described above and filling formed gelatin sheaths. A lubricant such as talc, magnesium stearate and calcium stearate can be added to the powder mixture as an adjuvant before the filling operation; a glidant such as colloidal silica may be added to improve flow properties; a disintegrating or solubilizing agent may be added to improve the availability of the medicament when the capsule is ingested.

Tablets are made by preparing a powder mixture, granulating or slugging, adding a lubricant and disintegrant and pressing into tablets. A powder mixture is prepared by mixing the compound, suitably comminuted, with a diluent or base such as starch, sucrose, kaolin, dicalcium phosphate and the like. The powder mixture can be granulated by wetting with a binder such as syrup, starch paste, acacia mucilage or solutions of cellulosic or polymeric materials and forcing through a screen. An an alternative to granulating, the powder mixture can be run through the tablet machine and the resulting imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The medicaments can also be combined with free-flowing inert carriers and compressed into tablets directly without going through the granulating or slugging steps. A protective coating consisting of a sealing coat of shellac, coating of sugar or polymeric material and a polish coating of wax can be provided. Dyestuffs can be added to these coatings to distinguish different unit dosages.

Oral fluids such as syrups and elixirs can be prepared in unit dosage form so that a given quantity, e.g., a teaspoonful, contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle in which it is insoluble.

Fluid unit dosage forms for parenteral administration can be prepared by suspending or dissolving a measured amount of the compound in a nontoxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration.

In general, satisfactory results both in human medicine and in veterinary medicine are achieved upon administration of the active compounds in total daily doses of from about 8 to about 500, preferably 30 to 250, mg/kg of body weight, optionally in the form of several individual administrations. However, it may be necessary to deviate from these dosage ranges and in particular to do so as a function of the condition and body weight of the patient being treated, the nature and severity of the illness, the nature of the composition, the route of administration, and the time or interval of the administration. In some cases, less than the above-mentioned amount is satisfactory, while in other cases the upper limit must be exceeded. The particular dosage which is optimum and the method of administration should, of course, be determined by a professional on the basis of his expert knowledge.

The compounds can also be used as a feedstuff additive in which compounds are administered in the usual manner together with the feedstuff or the feedstuff preparations, or with the drinking water. In this way, an infection by Gram negative of Gram positive bacteria can be prevented and, equally, better utilization of the feedstuff can be achieved.

The antimycotic activity and the powerful antibacterial effects coupled with oral resorbability can be readily observed in recognized in vitro models. As will be seen hereafter, the compounds have a broad spectrum of antimycotic action and a pronounced action peak against molds and Pityrosporum ovale. Particularly in the case of molds, MIC values are, for a comparable test method, better by a factor of 10 than for clotrimazol and better by up to a factor of 100 than for nystatin, pimaricin, amphotericin B and griseofulvin.

Their antibacterial effects is superior to other known azole derivatives, as well as to the above-mentioned antimicrobial agents, since the new compounds are also active against Gram negative bacteria.

A. Antimycotic activity, in vitro.

The MIC values of some compounds against important classes of fungi are listed in the table which follows.

The in vitro tests were carried out in a series dilution test with germ inocula averaging $5 \times 10^4$ germs/ml of substrate. The nutrient media used were (a) for dermatophytes and molds Sabouraud's milieu d'épreuve,
(b) for yeasts: meat extract-glucose bouillon,
(c) for Pytrosporum ovale: Abbe medium, and
(d) for biphase fungi in the yeast phase: Francis's blood agar.

The incubation temperatures were 28° C. for dermatophytes, yeasts and molds and 37° C. for biphase fungi; the incubation time was 24–96 hours.

Table A:

Antimycotic activity in vitro

| Active compound | MIC values in γ/ml of nutrient medium, for | | | | | |
|---|---|---|---|---|---|---|
| | Trichophyton mentagrophytes | Candida albicans | Pityrosporum ovale | Aspergillus fumigatus | penicillium | Histoplasma |
| biphenyl-CH(phenyl)-imidazole | <1 | 4 | 1 | <0.1 | <0.1 | 4 |
| biphenyl-CH(2-Cl-phenyl)-imidazole | <1 | 2 | 1 | <0.1 | <0.1 | 4 |
| biphenyl-CH(3-Cl-phenyl)-imidazole | 2 | 1 | 1 | <0.1 | <0.1 | 2 |
| phenoxyphenyl-CH(2-Cl-phenyl)-imidazole | 16 | 8 | 1 | <0.1 | <0.1 | 2 |

B. Antibacterial activity in vitro

The in vitro tests were carried out by the plast test. In this, the bacteria were cast with the agar, at a concentration of 5 × 10³/plate. The concentration in the plate which showed no formation of colonies is the MIC. The nutrient medium has the following composition:

| | |
|---|---|
| Proteose peptone | 10 g |
| Veal extract | 10 g |

-continued

| | |
|---|---|
| Dextrose | 2 g |
| NaCl | 3 g |
| Disodium phosphate | 2 g |
| Na acetate | 1 g |
| Adenine sulphate | 0.01 g |
| Guanine hydrochloride | 0.01 g |
| Uracil | 0.01 g |
| Xanthine | 0.01 g |
| Agar | 12.0 g |
| pH 7.4 | 1,000 ml aqua dest. |

Table B:

Antibacterial activity in vitro

| Active compound | MIC values for | | | | | |
|---|---|---|---|---|---|---|
| | Streptococcus pyogenes W | Staphylococcus aureus 133 | E-Coli A 261 | Pseudomonas aerug. B | Proteus vulgaris 1017 | Klebsiella 8085 |
| biphenyl-CH(phenyl)-imidazole | 10–20 | 8 | — | — | 128 | 128 |
| biphenyl-CH(2-Cl-phenyl)-imidazole | 128 | 8 | 256 | 256 | 128 | 128 |

Table B:-continued

Antibacterial activity in vitro

| Active compound | MIC values for | | | | | |
|---|---|---|---|---|---|---|
| | Streptococcus pyogenes W | Staphylococcus aureus 133 | E-Coli A 261 | Pseudomonas aerug. B | Proteus vulgaris 1017 | Klebsiella 8085 |
| (biphenyl-CH(imidazolyl)-C₆H₄-Cl structure) | 10 | 8 | — | — | — | — |
| (biphenyl-CH(imidazolyl)-C₆H₄-Cl structure, m-Cl) | 128 | 8 | — | — | — | — |
| (biphenyl-CH(imidazolyl)-C₆H₄-C(CH₃)₃ structure) | 128 | 8 | — | 256 | 128 | 128 |

EXAMPLE 1

A. (Biphenyl-4-yl)-phenyl-carbinol

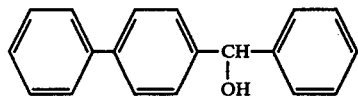

38.8 g (0.15 mol) of 4-phenylbenzophenone are dissolved in 200 ml of ethanol and 3 g (0.075 mol) of sodium borohydride are added. After heating for 15 hours under reflux, and allowing to cool, the reaction mixture is hydrolyzed with water containing a little hydrochloric acid. The solid thereby produced is purified by recrystallization from ethanol. 36 g (89% of theory) of (biphenyl-4-yl)-phenyl-carbinol [alternatively named as diphenyl-phenyl carbinol or α-(biphenyl-4-yl)benzylalcohol] of melting point 72°–73° C. are obtained.

B. (Biphenyl-4-yl)-imidazol-1-yl-phenylmethane

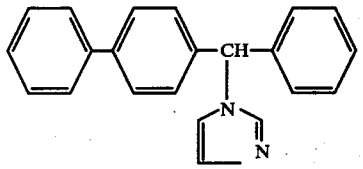

13.6 g (0.2 mol) of imidazole are dissolved in 150 ml of acetonitrile and 3.5 ml of thionyl chloride are added at 10° C. 13 g (0.05 mol) of (biphenyl-4-yl)-phenyl-carbinol are added to the solution of thionyl-bis-imidazole thus obtained. After standing for 15 hours at room temperature, the solvent is removed by distillation in vacuo. The residue is taken up in chloroform and the solution is washed with water. The organic phase is collected, dried over sodium sulfate and filtered and the solvent is distiller off in vacuo. The oily residue is dissolved in ethyl acetate and freed from insoluble, resinous constituents by filtration. The solvent is again distilled off in vacuo and the residue is purified by recrystallization from acetonitrile. 8.7 g (56% of theory) of (biphenyl-4-yl)-imidazol-1-yl-phenylmethane [alternatively named as diphenyl-imidazolyl-(1)-phenyl-methane or as 1-(α-biphenyl-4-ylbenzyl)imidazole] of melting point 142° C. are obtained.

EXAMPLE 2

In a similar fashion to that described in Example 1, from (biphenyl-4-yl)-2-chlorophenylcarbinol, (biphenyl-4-yl)-4-chlorophenylcarbinol, (biphenyl-4-yl)-3-chlorophenylcarbinol, (biphenyl-4-yl)-4-tert.-butyl-phenylcarbinol, and (4-phenoxyphenyl)-2-chlorophenylcarbinol, the following final compounds are respectively obtained: (biphenyl-4-yl)-imidazol-1-yl-(2-chlorophenyl)-methane, m.p. 90° C.; (biphenyl-4-yl)-imidazol-1-yl-(4-chlorophenyl)methane as an oil; (biphenyl-4-yl)-imidazol-1yl-(3-chlorophenyl)methane as an oil; (biphenyl-4-yl)-imidazol-1-yl-(4-tert.-butylphenyl)-methane as an oil; and (4-phenoxyphenyl-)imidazol-1-yl-(2-chlorophenyl)methane as an oil.

EXAMPLE 3

167 g (0.6 mol) of biphenyl-4-yl-phenyl-chloromethane [alternatively named as diphenyl-phenyl-chloromethane or as α-(biphenyl-4-yl)benzyl chloride] and 92 g (0.66 mol) of trimethylsilylimidazole, dissolved in 500 ml of acetonitrile, are heated under reflux for 15 hours. After distilling off the solvent, the crystalline residue is purified by recrystallization from ethyl acetate. 97 g (52% of theory) of (biphenyl-4-yl)-imidazol-1-yl-phenylmethane of melting point 142° C. are obtained.

EXAMPLE 4

By substituting α-(biphenyl-4-yl)-2-chlorobenzyl chloride, α-(biphenyl-4-yl)-4-chlorobenzyl chloride, α-(biphenyl-4-yl)-3-chlorobenzyl chloride, α-(biphenyl- 4-yl)-4-tert.-butylbenzyl chloride and α-(4-phenoxyphenyl)-2-chlorobenzyl chloride for the starting material of Example 3, there are respectively obtained the final compounds set forth in Example 2.

EXAMPLE 5

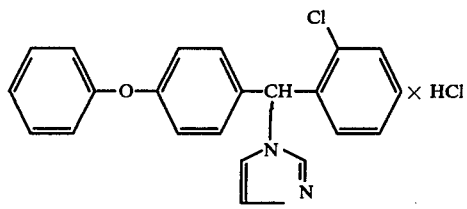 × HCl 32.9 g (0.1 mol) of (4-phenoxyphenyl)-(2-chlorophenyl)-chloromethane (alternatively named as α-(4-phenoxyphenyl)-2-chlorobenzyl chloride) and 6.8 g (0.1 mol) of imidazole are heated for 2 hours to 120° C. with stirring. After cooling, the glassy mass is dissolved in acetone and the solution is stirred with diisopropyl ether. 40 g (100% of theory) of (2-chlorophenyl)-imidazolyl-1-yl-(4-phenoxypphenyl)-methane as the hydrochloride of melting point 150° C. are obtained.

EXAMPLE 6

A. (2-Chlorophenyl)-(biphenyl-4-yl)-chloromethane

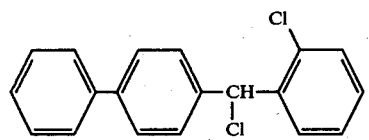

290 g (0.985 mol) of 2-chlorophenyl-(biphenyl-4-yl)-carbinol are dissolved in 1,000 ml of benzene and a solution of 144 ml (2 mols) of thionyl chloride in 400 ml of benzene is added slowly at 40° C. with stirring. The reaction mixture is heated under reflux for 15 hours. The solvent is distilled off in vacuo and the residue is stirred with 500 ml of petroleum ether. The crystals produced are filtered off and purified by recrystallization from ethanol. 36 g (89% of theory) of (2-chlorophenyl)-(biphenyl-4-yl)-chloromethane [alternatively named as α-(biphenyl-4-yl)-2l-chlorobenzyl chloride] of melting point 80° C. are obtained.

B. (2-Chlorophenyl)-imidazol-1-yl-(biphenyl-4-yl)methane

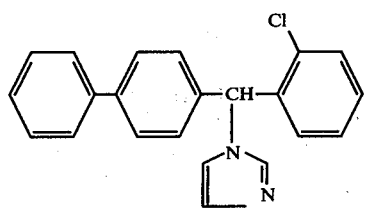

A solution of 13.6 g (0.2 mol) of imidazole in 100 ml of acetonitrile is added dropwise to a suspension of 10.8 g (0.13 mol) of sodium methylate in 200 ml of acetonitrile. The resulting sodium imidazole is filtered off and suspended in 300 ml of acetonitrile, and 31.3 g (0.1 mol) of (2-chlorophenyl)-(biphenyl-4-yl)-chloromethane are added. After heating for 24 hours to 80° C., the mixture is allowed to cool, and is filtered. The filtrate is freed from the solvent by distilling the latter off in vacuo. The oil which remains is dissolved in ethyl acetate and the solution is washed with water, dried over sodium sulfate, filtered and freed from the solvent in vacuo. The oily residue is dissolved in chloroform and chromatographed on a silica gel column. After separating off a chloroform fraction containing a compound of melting point 150° C., the chloroform fraction containing desired end product is obtained. After distilling off the solvent, 10.7 g (31% of theory) of (2-chlorophenyl-)imidazol-1-yl-(biphenyl-4-yl)-methane of melting point 90° C. are obtained.

In a like fashion, by substituting the second through the fifth of the substituted benzyl chlorides recited in Example 4, the second through the fifth final compounds recited in Example 2 are respectively obtained.

EXAMPLE 7

Treatment of (biphenyl-4-yl)-imidazol-1-yl-phenyl-methane with the appropriate acids yields the following salts:

| | |
|---|---|
| hydrochloride | m.p. 220° C |
| sulfate | m.p. 130° C |
| phosphate | m.p. 190° C |
| nitrate | m.p. 186° C |
| acetate | m.p. 150° C |
| lactate | m.p. 130° C |
| salicylate | oil |
| 1,5-naphthalene-disulfonate | m.p. 260° C |

EXAMPLE 8

The following compounds are prepared according to the methods described in Examples 1–6 from the correspondingly α-substituted benzyl alcohols or α-substituted benzyl chlorides:

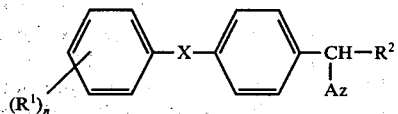

| R¹ | n | X | Az | R² | m.p. |
|---|---|---|---|---|---|
| H | 1 | — | imidazol-1-yl | 3-methylphenyl | 200° C |
| 4-Cl | 1 | — | imidazol-1-yl | 3-chlorophenyl | 114° C |
| 4-Cl | 1 | — | imidazol-1-yl | 2-chlorophenyl | 130° C |
| H | 1 | —O— | imidazol-1-yl | 4-chlorophenyl | oil |
| H | 1 | — | pyrazol-1-yl | phenyl | 90° C |
| H | 1 | — | 1,2,4-triazol-1-yl | phenyl | 169° C |
| H | 1 | —S— | imidazol-1-yl | phenyl | 72° C |

EXAMPLE 9

In accordance with the methods described in Examples 1–6, the following compounds are prepared from the correspondingly α-substituted benzyl alcohols or α-substituted benzyl chlorides:

| R¹ | n | X | Az | R² |
|---|---|---|---|---|
| H | 1 | — | imidazol-1-yl | tert.-butyl |
| H | 1 | O | imidazol-1-yl | tert.-butyl |
| 4-Cl | 1 | — | imidazol-1-yl | n-propyl |
| H | 1 | — | imidazol-1-yl phenyl | 3-trifluoromethyl- |
| 2,4,6-Cl₃ | 3 | — | imidazol-1-yl | phenyl |
| 3-C₂H₅ | 1 | — | imidazol-1-yl | phenyl |
| H | 1 | —SO₂— | imidazol-1-yl | phenyl |
| 2-benzyl | 1 | — | imidazol-1-yl | 2-chlorophenyl |
| H | 1 | — | imidazol-1-yl | 2,5-dichlorophenyl |
| H | 1 | — | pyrazol-1-yl | 2-chlorophenyl |

-continued

| R¹ | n | X | Az | R² |
|---|---|---|---|---|
| H | 1 | 0 | pyrazol-1-yl | phenyl |
| 3-CH₃ | 1 | — | 1,2,4-triazol-1-yl | phenyl |
| H | 1 | — | 1,2,4-triazol-1-yl | 2-chlorophenyl |
| 4-Cl | 1 | — | 1,2,4-triazol-4-yl | phenyl |

What is claimed is:

1. A compound selected from the group consisting of an imidazole of the formula:

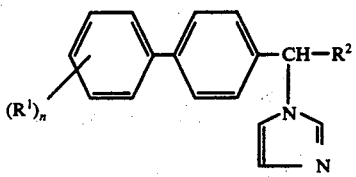

and the pharmaceutically acceptable nontoxic salts thereof, wherein
R¹ is hydrogen, halo, lower alkyl; lower alkoxy, halo(lower alkyl); or phenyl(lower alkyl);
R² is lower alkyl, phenyl or phenyl substituted with one or two substituents independently selected from the group consisting of lower alkyl, halo and halo(lower alkyl); and
n is 1, 2 or 3.

2. A compound according to claim 1 wherein R¹ is hydrogen; chloro; bromo; lower alkyl; or benzyl.

3. A compound according to claim 1 wherein R² is lower alkyl; phenyl; or phenyl substituted with one or two substituents selected from the group consisting of chloro, bromo, lower alkyl or trifluoromethyl.

4. A compound according to claim 1 wherein
R¹ is hydrogen or chloro;
n is 1;
R² is phenyl, chlorophenyl or (lower alkyl)phenyl.

5. A compound according to claim 1 wherein said substituted azol-1-ylmethane is of the formula

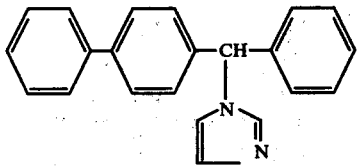

6. A compound according to claim 1 wherein said substituted azol-1-ylmethane is of the formula

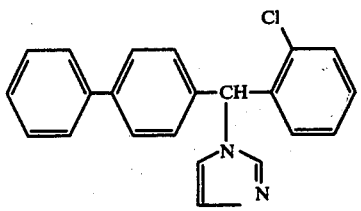

7. A compound according to claim 1 wherein
R¹ is hydrogen or chloro; and
R² is phenyl, chlorophenyl or(lower alkyl)phenyl.

8. A compound according to claim 1 which is a pharmaceutically acceptable, nontoxic salt selected from the group consisting of the hydrochloride, the hydrobromide, phosphate, nitrate, sulfate, acetate, maleate, succinate, fumarate, tartrate, citrate, salicylate, sorbate, lactate and 1,5-naphthalenedisulfonate.

9. A compound according to claim 1 which is a pharmaceutically acceptable, nontoxic salt of a compound of the formula

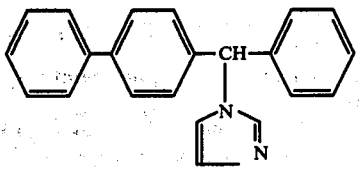

wherein said salt is selected from the group consisting of the hydrochloride, phosphate, nitrate, sulfate, acetate, lactate, salicylate and 1,5-naphthalene disulfonate.

10. A compound according to claim 1 wherein
R¹ is hydrogen;
n is 1; and
R² is 3-methylphenyl.

11. A compound according to claim 1 wherein
R¹ is 4-chloro;
n is 1; and
R² is 3-chlorophenyl.

12. A compound according to claim 1 wherein
R¹ is 4-chloro;
n is 1; and
R² is 2-chlorophenyl.

13. A compound according to claim 1 wherein
R¹ is hydrogen;
n is 1; and
R² is tert.-butyl.

14. A compound according to claim 1 wherein
R¹ is 4-chloro;
n is 1; and
R² is n-propyl.

15. A compound according to claim 1 wherein
R¹ is hydrogen;
n is 1; and
R² is 3-trifluoromethylphenyl.

16. A compound according to claim 1 wherein
R¹ is chloro;
n is 3, said three chloro atoms being in the 2-, 4- and 6-positions of the depicted phenyl ring; and
R² is phenyl.

17. A compound according to claim 1 wherein
R¹ is 3-ethyl;
n is 1; and
R² is phenyl.

18. A compound according to claim 1 wherein
R¹ is 2-benzyl;
n is 1; and
R² is 2-chlorophenyl.

19. The compound according to claim 1 wherein
R¹ is hydrogen;
n is 1; and
R² is 2,5-dichlorophenyl.

20. A pharmaceutical composition useful for treating mycoses and bacterial infections in humans and animals which comprises an antimycotically effective amount or an antibacterially effective amount of a compound selected from the group consisting of an imidazole of the formula:

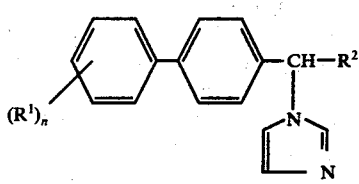

and the pharmaceutically acceptable, nontoxic salts thereof, wherein
  R¹ is hydrogen; halo; lower alkyl; lower alkoxy; halo(lower alkyl); or phenyl(lower alkyl);
  R² is lower alkyl; phenyl; or phenyl substituted by one or two substituents independently selected from the group consisting of lower alkyl, halo, and halo(lower alkyl); and
  n has a value of from 1 to 3,
in combination with a pharmaceutically acceptable, nontoxic, inert diluent or carrier.

21. A composition according to claim 20 wherein R¹ is hydrogen; chloro; bromo; lower alkyl; or benzyl.

22. A composition according to claim 20 wherein R² is lower alkyl; phenyl; or phenyl substituted with one or two substitutents selected from the group consisting of chloro, bromo, lower alkyl or trifluoromethyl.

23. A composition according to claim 20 wherein the compound is of the formula

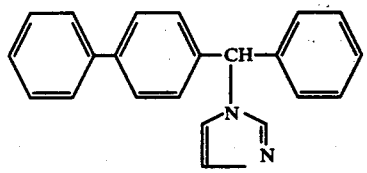

24. A composition according to claim 20 wherein the compound is of the formula

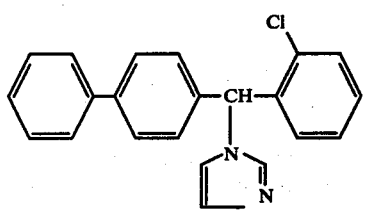

25. A composition according to claim 20 wherein the compound is a pharmaceutically acceptable, nontoxic salt selected from the group consisting of the hydrochloride, the hydrobromide, phosphate, nitrate, sulfate, acetate, maleate, succinate, fumarate, tartrate, citrate, salicylate, sorbate, lactate and 1,5-naphthalenedisulfonate.

26. A composition according to claim 20 wherein the compound is a pharmaceutically acceptable, nontoxic salt of the imidazole of the formula

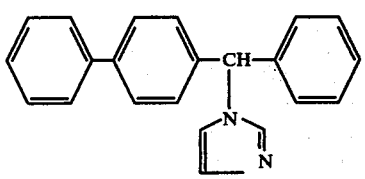

wherein said salt is selected from the group consisting of the hydrochloride, phosphate, nitrate, sulfate, acetate, lactate, salicylate and 1,5-naphthalene disulfonate.

27. A composition according to claim 20 wherein
  R¹ is hydrogen;
  n is 1; and
  R² is 3-methylphenyl.

28. A composition according to claim 20 wherein
  R¹ is 4-chloro;
  n is 1; and
  R² is 3-chlorophenyl.

29. A composition according to claim 20 wherein
  R¹ is 4-chloro;
  n is 1 and
  R² is 2-chlorophenyl.

30. A composition according to claim 20 wherein
  R¹ is hydrogen;
  n is 1; and
  R² is tert.-butyl.

31. A composition according to claim 20 wherein
  R¹ is 4-chloro;
  n is 1; and
  R² is n-propyl.

32. A composition according to claim 20 wherein
  R¹ is hydrogen;
  n is 1; and
  R² is 3-trifluoromethylphenyl.

33. A composition according to claim 20 wherein
  R¹ is chloro;
  n is 3, said three chloro atoms being in the 2-, 4- and 6-positions of the depicted phenyl ring; and
  R² is phenyl.

34. A composition according to claim 20 wherein
  R¹ is 3-ethyl;
  n is 1; and
  R² is phenyl.

35. A composition according to claim 20 wherein
  R¹ is 2-benzyl;
  n is 1; and
  R² is 2-chlorophenyl.

36. A composition according to claim 20 wherein
  R¹ is hydrogen;
  n is 1; and
  R² is 2,5-dichlorophenyl.

37. A method of treating mycoses and bacterial infections in humans and animals which comprises administering to a human or animal in need thereof an effective amount of a pharmaceutical composition which comprises an antimycotically effective amount or an antibacterially effective amount of a compound selected from the group consisting of an imidazole of the formula:

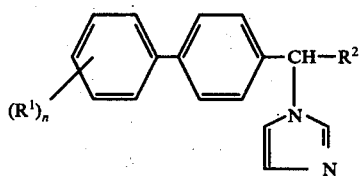

and the pharmaceutically acceptable, nontoxic salts thereof, wherein
  R¹ is hydrogen; halo; lower alkyl; lower alkoxy; halo(lower alkyl); or phenyl(lower alkyl);
  R² is lower alkyl; phenyl; or phenyl substituted by one or two substituents independently selected from the group consisting of lower alkyl, halo, and halo(lower alkyl);

$n$ has a value of from 1 to 3, in combination with a pharmaceutically acceptable, nontoxic, inert diluent or carrier.

38. A method according to claim 37 wherein $R^1$ is hydrogen; chloro; bromo; lower alkyl; or benzyl.

39. A method according to claim 37 wherein $R^2$ is lower alkyl; phenyl; or phenyl substituted with one or two substituents selected from the group consisting of chloro, bromo, lower alkyl or trifluoromethyl.

40. A method according to claim 37 wherein the compound is of the formula

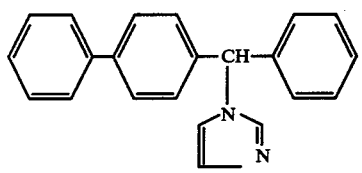

41. A method according to claim 37 wherein the compound is of the formula

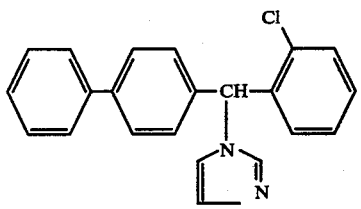

42. A method according to claim 37 wherein the compound is a pharmaceutically acceptable, non-toxic salt selected from the group consisting of the hydrochloride, the hydrobromide, phosphate, nitrate, sulfate, acetate, maleate, succinate, fumarate, tartrate, citrate, salicylate, sorbate, lactate and 1,5-naphthalenedisulfonate.

43. A method according to claim 37 wherein the compound is a pharmaceutically acceptable, nontoxic salt of the imidazole of the formula

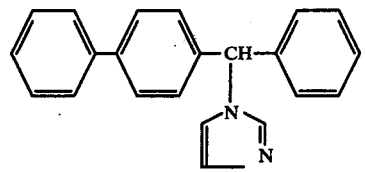

wherein said salt is selected from the group consisting of the hydrochloride, phosphate, nitrate, sulfate, acetate, lactate, salicylate and 1,5-naphthalene disulfonate.

44. A method according to claim 37 wherein
$R^1$ is hydrogen;
$n$ is 1; and
$R^2$ is 3-methylphenyl.

45. A method according to claim 37 wherein
$R^1$ is 4-chloro;
$n$ is 1; and
$R^2$ is 3-chlorophenyl.

46. A method according to claim 37 wherein
$R^1$ is 4-chloro;
$n$ is 1; and
$R^2$ is 2-chlorophenyl.

47. A method according to claim 37 wherein
$R^1$ is hydrogen;
$n$ is 1; and
$R^2$ is tert.-butyl.

48. A method according to claim 37 wherein
$R^1$ is 4-chloro;
$n$ is 1; and
$R^2$ is n-propyl.

49. A method according to claim 37 wherein
$R^1$ is hydrogen;
$n$ is 1; and
$R^2$ is 3-trifluoromethylphenyl.

50. A method according to claim 37 wherein
$R^1$ is chloro;
$n$ is 3, said three chloro atoms being in the 2-, 4- and 6-positions of the depicted phenyl ring; and
$R^2$ is phenyl.

51. A method according to claim 37 wherein
$R^1$ is 3-ethyl;
$n$ is 1; and
$R^2$ is phenyl.

52. A method according to claim 37 wherein
$R^1$ is 2-benzyl;
$n$ is 1; and
$R^2$ is 2-chlorophenyl.

53. A method according to claim 37 wherein
$R^1$ is hydrogen;
$n$ is 1; and
$R^2$ 2,5-dichlorophenyl.

* * * * *